United States Patent
Kjeldsen et al.

(10) Patent No.: US 10,945,627 B2
(45) Date of Patent: Mar. 16, 2021

(54) SYSTEMS AND METHODS FOR SUPER-RESOLVING ELECTROMAGNETIC LOCALIZATION AND CAUSALITY

(71) Applicant: TRUUST NEUROIMAGING, Inc., San Francisco, CA (US)

(72) Inventors: Henrik D. Kjeldsen, Skoedstrup (DK); Lars H. Bredvig, Egaa (DK)

(73) Assignee: TRUUST NEUROIMAGING, INC., San Francisco, CA (US)

( * ) Notice: Subject to any disclaimer, the term of this patent is extended or adjusted under 35 U.S.C. 154(b) by 337 days.

(21) Appl. No.: 16/017,400

(22) Filed: Jun. 25, 2018

(65) Prior Publication Data

US 2019/0008408 A1    Jan. 10, 2019

Related U.S. Application Data

(63) Continuation of application No. PCT/US2017/014430, filed on Jan. 20, 2017.
(Continued)

(51) Int. Cl.
*A61B 5/0478* (2006.01)
*A61B 5/00* (2006.01)
(Continued)

(52) U.S. Cl.
CPC ........ *A61B 5/0478* (2013.01); *A61B 5/04001* (2013.01); *A61B 5/04008* (2013.01);
(Continued)

(58) Field of Classification Search
CPC ............. A61B 5/04001; A61B 5/4064; A61B 5/0478; A61B 5/0476; A61B 5/7235;
(Continued)

(56) References Cited

U.S. PATENT DOCUMENTS

| | | | | |
|---|---|---|---|---|
| 2007/0239059 A1* | 10/2007 | McIver | ................. | A61B 5/745 600/544 |
| 2013/0223709 A1* | 8/2013 | Wagner | ............... | A61B 5/0033 382/128 |
| 2013/0231553 A1* | 9/2013 | Tucker | ................ | A61B 5/0478 600/411 |

OTHER PUBLICATIONS

Kjeldsen, H. et al., "Near-Field electromagnetic Holography for high-resolution analysis of network interactions in neuronal tissue," Journal of Neuroscience Methods 2015; http://dx.doi.or/10.1016/ijneumeth.2015.05.016, 26 pages. (Year: 2015).*
(Continued)

*Primary Examiner* — Christine H Matthews
*Assistant Examiner* — Joshua Daryl D Lannu
(74) *Attorney, Agent, or Firm* — Cooley LLP (57) ABSTRACT

Systems and methods are described for super-resolving electromagnetic localization by obtaining electric field data and/or magnetic field data captured over a period of time by at least one multi-channel recording device having a first resolution, applying holographic backpropagation constrained by sparsity approximation and/or low-rank approximation in a near-field and/or a far-field to the captured data, reconstructing electromagnetic energy flow information at a second resolution in one iteration, the second resolution being higher than the first resolution in at least two of three spatial dimensions, and generating data indicating an energy source location, an energy sink location, and/or a causality relation based on the electromagnetic energy flow information at the second resolution.

18 Claims, 6 Drawing Sheets

Related U.S. Application Data (60) Provisional application No. 62/281,519, filed on Jan. 21, 2016.

(51) Int. Cl.

| | | |
|---|---|---|
| *A61N 1/05* | (2006.01) | |
| *G01R 33/32* | (2006.01) | |
| *A61B 5/0476* | (2006.01) | |
| *A61B 5/04* | (2006.01) | |
| *G06K 9/00* | (2006.01) | |

(52) U.S. Cl.
CPC .......... *A61B 5/0476* (2013.01); *A61B 5/4064* (2013.01); *A61B 5/7235* (2013.01); *A61N 1/0529* (2013.01); *G01R 33/323* (2013.01); *G06K 9/0057* (2013.01)

(58) Field of Classification Search
CPC ............. A61B 5/04008; G01R 33/323; A61N 1/0529; G06K 9/0057
See application file for complete search history.

(56) References Cited

OTHER PUBLICATIONS

Kjeldsen, H. et al., "Near-Field electromagnetic Holography for high-resolution analysis of network interactions in neuronal tissue," Journal of Neuroscience Methods 2015; http://dx.doi.or/10.1016/j.jneumeth.2015.05.016, 26 pages.

Liu, J. et al., "Tensor Completion for Estimating Missing Values in Visual Data," International Conference on Computer Vision 2009; http://pages.cs.wisc.edu/~ji-liu/paper/Ji-ICCV09.pdf, 14 pages.

International Search Report and Written Opinion dated Apr. 12, 2017 for International Application No. PCT/US2017/014430, 9 pages.

* cited by examiner

FIG. 4A  POTENTIAL AND ELECTRIC FIELD

FIG. 4B  POTENTIAL, ELECTRIC AND MAGNETIC FIELD

FIG. 4C  POTENTIAL, ELECTRIC, MAGNETIC AND POYNTING VECTORS FIELD

SYSTEMS AND METHODS FOR SUPER-RESOLVING ELECTROMAGNETIC LOCALIZATION AND CAUSALITY

CROSS-REFERENCE TO RELATED APPLICATIONS

This application is a continuation of International Patent Application No. PCT/US2017/014430, filed Jan. 20, 2017, entitled "Systems and Methods for Super-Resolving Electromagnetic Localization and Causality," which claims priority to and the benefit of U.S. Provisional Patent Application No. 62/281,519, filed Jan. 21, 2016, entitled "Systems and Methods for Super-Resolving Electromagnetic Localization and Causality," both of which are incorporated herein by reference in their entirety.

TECHNICAL FIELD

The present disclosure generally relates to systems and methods for recording and analyzing electrical and/or magnetic signals. More specifically, the present disclosure to improved systems and methods for electromagnetic neuroimaging and analysis of neural activity.

BACKGROUND

Electromagnetic neuroimaging modalities include, for example, multi-electrode or microelectrode arrays (MEAs), electroencephalography (EEG), electrocorticography (ECoG), and magnetoencephalography (MEG). An MEA comprises multiple plates for connecting neurons to electronic circuitry for receiving and/or delivering electrical neural signals; and in addition to in vitro use, an MEA may be implanted for in vivo use. EEG involves the placement of electrodes along the scalp to measure voltage fluctuations resulting from ionic current within the neurons of the brain, particularly types of neural oscillations (i.e., "brain waves") in EEG signals. In ECoG or intracranial electroencephalography (iEEG), electrodes are placed directly on an exposed surface of the brain to record electrical activity from the cerebral cortex. MEG involves mapping brain activity by recording magnetic fields produced by electrical currents occurring naturally in the brain, using very sensitive magnetometers (e.g., arrays of superconducting quantum interference devices (SQUIDs)).

The challenge posed by such modalities is an inverse problem without a unique solution: to estimate model parameters, such as source locations and timing of electric activity within a brain, from measured data (e.g., induced electrical neural signals, voltage fluctuations on the brain surface, voltage fluctuations outside the head, and/or magnetic fields outside the head).

Estimated source locations may be combined with, for example, magnetic resonance imaging (MRI) images, to create electric source images (ESIs) and/or magnetic source images (MSIs) and image sequences of neural activity at resolutions corresponding to the resolution of the recording equipment, or at "increased" resolutions by various forms of interpolation, but without increasing the actual information content.

SUMMARY

The inventors recognized and appreciated that conventional computer reconstructions of neural activity at a depth in neural tissue are inherently resolution limited because the inverse problem of reconstructing three-dimensional (3D) information from two-dimensional (2D) manifold recordings has been ill-posed.

For example, conventional estimates of neural causality (i.e., which source locations influence other locations, when, and by how much) are based on statistical measures of the variance of neural signals recorded at multiple locations. These statistical measures are inherently far-removed from the underlying physical and biological activity. As the number of unique recording locations (i.e., the resolution) increase, accurate solutions become computationally intractable, and further approximations must be used. Furthermore, conventional methods are unable to distinguish between contact-based neurotransmission types, such as chemical synapses, electrical synapses (e.g., gap junctions), and ephaptic connections. Current estimates of neuro-computation are based directly on neural activity without the possibility to distinguish activity that does not contribute to actual neuro-computation.

The inventors further recognized and appreciated that, in general, understanding and modification of neural processes depend on localization of neural sources, their causality relations, and their contributions to neural computation. One application of neuroimaging is the localization of focal points of neural seizure activity in clinical preparation for epileptic brain-surgery. The goal of the surgery is to remove the focal points. However, an important constraint—to minimize side-effects—is to remove as little neural tissue as possible. Thus, the resolution of the neuroimaging modality is critical, but resolution is currently limited by physical size/space constraints on the recording equipment. Another important constraint is to remove only those focal points that originate epileptic seizures. That is, a first focal point may not originate seizures—and does not need to be removed—but, instead, be entirely driven by a second focal point that does originate seizures. Thus, estimates of neural causality are critical for determining which focal locations drive seizures.

The present disclosure provides systems and methods to provide significantly improved neural source localization, neuro-causality relations, and/or neuro-computation estimates by increasing resolution via holographic reconstruction constrained by sparsity and/or low-rank approximation in both near- and far-fields as well as electromagnetic energy-based measures and their derivatives in accordance with some embodiments.

In one embodiment, a system for super-resolving electromagnetic neuroimaging includes at least one multi-channel recording device for capturing electric field data and/or magnetic field data in neural tissue of a subject over a period of time, the at least one multi-channel recording device having a first resolution, at least one memory to record the captured data and to store processor executable instructions, and at least one processor coupled to the at least one multi-channel recording device and the at least one memory. Upon execution of the processor executable instructions by the at least one processor, the at least one processor applies holographic backpropagation to the captured data, the holographic backpropagation constrained by sparsity approximation or low-rank approximation in a near-field and/or a far-field, reconstructs electromagnetic energy flow information at a second resolution in one iteration, the second resolution being higher than the first resolution in at least two of three spatial dimensions, and generates, based on the electromagnetic energy flow information at the second resolution, data indicating a neural energy source location, a neural energy sink location, and/or a neural causality relation. In an embodiment, the neural causality relation distinguishes contact-based neural transmission and field-based neural transmission.

In one embodiment, a system for super-resolving electromagnetic localization includes at least one multi-channel recording device for capturing electric field data and/or magnetic field data over a period of time, the at least one multi-channel recording device having a first resolution, at least one memory to record the captured data and to store processor executable instructions, and at least one processor coupled to the at least one multi-channel recording device and the at least one memory. Upon execution of the processor executable instructions by the at least one processor, the at least one processor applies holographic backpropagation to the captured data, the holographic backpropagation constrained by sparsity approximation or low-rank approximation in a near-field and/or a far-field, reconstructs electromagnetic energy flow information at a second resolution in one iteration, the second resolution being higher than the first resolution in at least two of three spatial dimensions, and generates, based on the electromagnetic energy flow information at the second resolution, data indicating an energy source location, an energy sink location, and/or a causality relation.

In another embodiment, a system for super-resolving electromagnetic localization includes at least one communication interface, at least one memory to record the captured data and to store processor executable instructions, and at least one processor coupled to the at least one communication interface and the at least one memory. Upon execution of the processor executable instructions by the at least one processor, the at least one processor obtains, via the at least one communication interface, electric field data and/or magnetic field data captured over a period of time by at least one multi-channel recording device, the at least one multi-channel recording device having a first resolution, applies holographic backpropagation to the captured data, the holographic backpropagation constrained by sparsity approximation or low-rank approximation in a near-field and/or a far-field, reconstructs electromagnetic energy flow information at a second resolution in one iteration, the second resolution being higher than the first resolution in at least two of three spatial dimensions; and generates, based on the electromagnetic energy flow information at the second resolution, data indicating an energy source location, an energy sink location, and/or a causality relation.

In one embodiment, a method for super-resolving electromagnetic neuroimaging includes obtaining electric field data and/or magnetic field data from neural tissue of a subject over a period of time by at least one multi-channel recording device, the at least one multi-channel recording device having a first resolution, applying, via at least one processor, holographic backpropagation to the captured data, the holographic backpropagation constrained by sparsity approximation and/or low-rank approximation in a near-field and/or a far-field, reconstructing, via the at least one processor, electromagnetic energy flow information at a second resolution in one iteration, the second resolution being higher than the first resolution in at least two of three spatial dimensions, and generating, via the at least one processor, data indicating a neural energy source location, a neural energy sink location, and/or a neural causality relation based on the electromagnetic energy flow information at the second resolution. In an embodiment, the neural causality relation distinguishes contact-based neural transmission and field-based neural transmission.

In another embodiment, a method for super-resolving electromagnetic localization includes obtaining electric field data and/or magnetic field data captured over a period of time by at least one multi-channel recording device, the at least one multi-channel recording device having a first resolution, applying holographic backpropagation to the captured data, the holographic backpropagation constrained by sparsity approximation and/or low-rank approximation in a near-field and/or a far-field, reconstructing electromagnetic energy flow information at a second resolution in one iteration, the second resolution being higher than the first resolution in at least two of three spatial dimensions, and generating data indicating an energy source location, an energy sink location, and/or a causality relation based on the electromagnetic energy flow information at the second resolution. In an embodiment, the method includes capturing, via the at least one multi-channel recording device, the electric field data and/or the magnetic field data.

In some embodiments, the at least one multi-channel recording device includes a near-field multi-channel recording device. In other embodiments, the at least one multi-channel recording device includes a far-field multi-channel recording device. The at least one multi-channel recording device may include a microelectrode array (MEA) device, an electroencephalography (EEG) device, an electrocorticography (ECoG) device, and/or a magnetoencephalography (MEG) device.

In some embodiments, the electromagnetic energy flow information includes at least one Poynting vector. The electromagnetic energy flow information may include a Poynting vector field. The causality relation may be a flow direction of the Poynting vector field.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the figures, described herein, are for illustration purposes only, and that the drawings are not intended to limit the scope of the disclosed teachings in any way. In some instances, various aspects or features may be shown exaggerated or enlarged to facilitate an understanding of the inventive concepts disclosed herein (the drawings are not necessarily to scale, emphasis instead being placed upon illustrating the principles of the teachings). In the drawings, like reference characters generally refer to like features, functionally similar and/or structurally similar elements throughout the various figures.

DETAILED DESCRIPTION

Following below are more detailed descriptions of various concepts related to, and embodiments of, improved systems and methods for imaging, and more particularly to improved systems and methods for neuroimaging and analysis of biological neural activity. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

According to some embodiments, electromagnetic neuroimaging systems and methods provide superior estimates of neural energy flow, neural causality relations, and/or neuro-computation in live neural tissue at resolutions significantly higher than the spatial resolution of the recording equipment. Significant improvements in clinical neuro-diagnosis and intervention planning may include, but are not limited to, (1) more accurate localization of focal points (e.g., for epileptic seizures, event-related potentials (ERPs), evoked potentials, and general activity); (2) better estimation of causal relations between localized focal points, and/or (3) earlier detection of neural changes, sometimes called biomarkers, linked to disease (e.g., brain tumors, epilepsy, traumatic brain injury), disorder (e.g. schizophrenia, autism, ADHD), and/or age-related cognitive deficits (e.g., dementia, Alzheimer's disease, Parkinson's disease). Increased resolution also implies significant improvement in the basis for brain-computer interfaces (BCI), in the scope and efficacy of neuro-feedback therapeutics, and in the prospect of data-mining the resulting data via machine learning, which is data volume driven (i.e., increased resolution dramatically increases the available data), and therefore the machine learning potential and statistical power. Increased resolution also implies significant improvement in targeting, tracking, and evaluation of neuro-stimulation, exemplified by transcranial magnetic or direct current stimulation.

New research opportunities stemming from increased neuroimaging resolution and, in particular, from new measures of neural activity may include, but are not limited to, (1) causality estimates from neural energy flow Poynting vector fields; (2) source and sink mapping based on neural energy source density; (3) neuro-computational estimates based on neural energy dissipation; and/or (4) measureable distinctions between contact-based and field-based neuro-transmission types.

According to some embodiments, super-resolution from far-field array recordings is combined with several new physical measures of neural energy flow (e.g., Poynting vector fields) and derivatives in live neural tissue.

Figure 1:
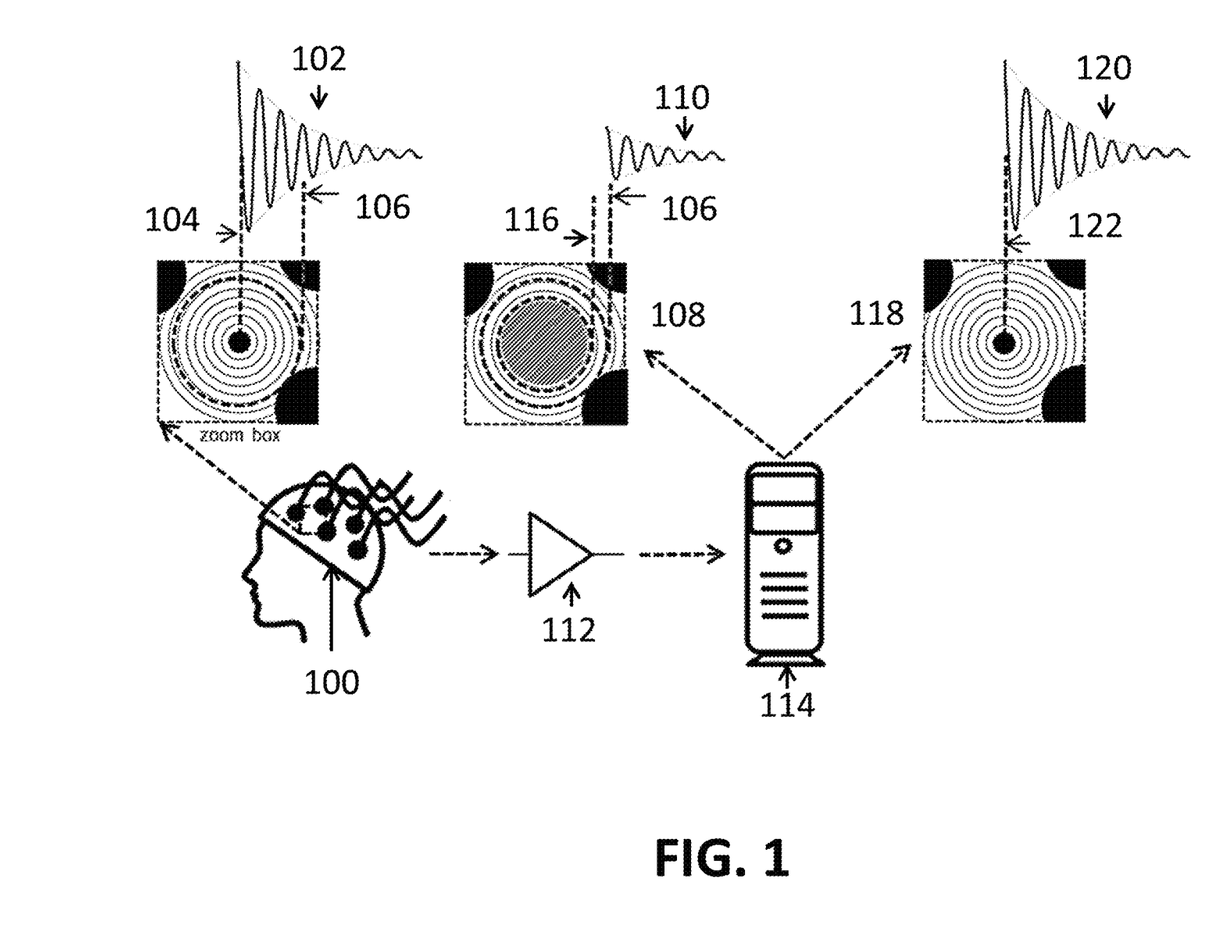
FIG. 1 is a flowchart illustrating the differences between conventional methods and a method for reconstructing a source location in accordance with some embodiments.

FIG. 1 is a flowchart illustrating the differences between conventional methods and a method for reconstructing a source location in accordance with some embodiments. In FIG. 1, a subject is prepared for recording by arranging an array 100 for sensing an electric field and/or a magnetic field (e.g., at least one of an MEA, an EEG and/or ECoG electrode array, and an MEG magnetometer array).

FIG. 1 illustrates a real signal 102 (e.g., a change in the electric field and/or magnetic field) with a real source location 104 and a near field limit 106. FIG. 1 also illustrates a conventional method 108 for estimating the real signal based on the recorded signal 110. The recorded signal 110 may be amplified 112 and/or pre-processed 114 using at least one digital computer. Pre-processing steps may include, but not limited to, rejection of bad channels (i.e., channels with no signal or excessive broadband noise), averaging, de-trending, partitioning, and filtering to, e.g., remove power grid noise at 50 hz and/or 60 hz (i.e., notch filtering) or emphasize bands of interest (i.e., bandpass filtering). However, due to the uncertainty of the source location 116 and the limits of far-field recording (i.e., near field limit 106), the conventionally recorded signal 110 fails to capture the near-field information and thus diverges substantially from the real signal 102 in FIG. 1.

FIG. 1 further illustrates a novel method 118 for obtaining a reconstructed signal 120 based on the recorded signal 110 and a reconstruction of the source location 122 and near-field information in accordance with some embodiments. Again, the recorded signal 110 may be amplified 112 and/or pre-processed 114 using at least one digital computer. Pre-processing steps may include, but not limited to, rejection of bad channels (i.e., channels with no signal or excessive broadband noise), averaging, de-trending, partitioning, and filtering to, e.g., remove power grid noise at 50 hz and/or 60 hz (i.e., notch filtering) and/or emphasize bands of interest (i.e., bandpass filtering).

According to some embodiments, the near-field information associated with the real signal is reconstructed by compressive sensing or low-rank tensor completion. Compressive sensing assumes signal sparsity and is generally a slow optimization process. Low-rank tensor completion assumes that the signal has a (tensor) low-rank approximation, and is generally a faster optimization process.

Super-resolution holographic backpropagation (covering both 2D-to-2D and 2D-to-3D cases) leverages the near-field information reconstructed in the previous step to reconstruct source information at high resolution both in 2D and 3D, and may itself be regularized by compressive sensing or low-rank tensor completion to prevent instability in the process. Holographic backpropagation may be carried out in time, frequency, wavelet, and/or mixed domains as long as no assumptions are made that neglect the near-field information.

In some embodiments, the system may be modeled in tensor form as:

$$y = Ax + N \qquad (1)$$

where y is the measured data, A is the sensing operator (conductivity and propagation model), x is the reconstructed plane and/or volume, and N is undefined noise. The measured data y has much fewer elements than the reconstructed plane and/or volume x. The objective is to solve for x under the assumption that x is either sparse or has a low-rank approximation.

The conductivity values of different brain regions may be well-known at a macro level, but may fail to capture conductivity values specific to a particular subset of brain cells or tissue. The conductivity values representing specific areas may be arranged (in what is commonly referred to as a "head model") according to simple models (e.g., concentric spheres), generic brain anatomy models, and/or models specific to one or more subjects (based on, e.g., MRI imaging of the subject(s) and/or histological staining of tissue samples from the subject(s)). More accurate head models may lead to better results in accordance with some embodiments.

The propagation model may be described using standard equations of electromagnetic propagation in media with conductivity values according to the conductivity model. In some embodiments, the propagation model may include terms accounting for inhomogeneity, non-linearity, absorption, etc. In other embodiments, the propagation model may be simplified and/or approximated. More accurate models of electromagnetic wave propagation may lead to better results in accordance with some embodiments.

Under the assumption that x is sparse or has a low-rank approximation, system (1) may be solved with high accuracy by numerical optimization. When the reconstructed plane and/or volume x is small, system (1) may be solved directly, e.g., by tensor rank optimization. The computational complexity of tensor rank grows exponentially with the size of x, so for realistic sizes of x, the solution of system (1) must be approximated, e.g., by tensor trace norm optimization and/or other relaxation schemes. As illustrated in FIG. 1, the reconstructed signal 120 includes near-field information and thus more closely matches the real signal 102 than the recorded signal 110 alone.

Figure 2:
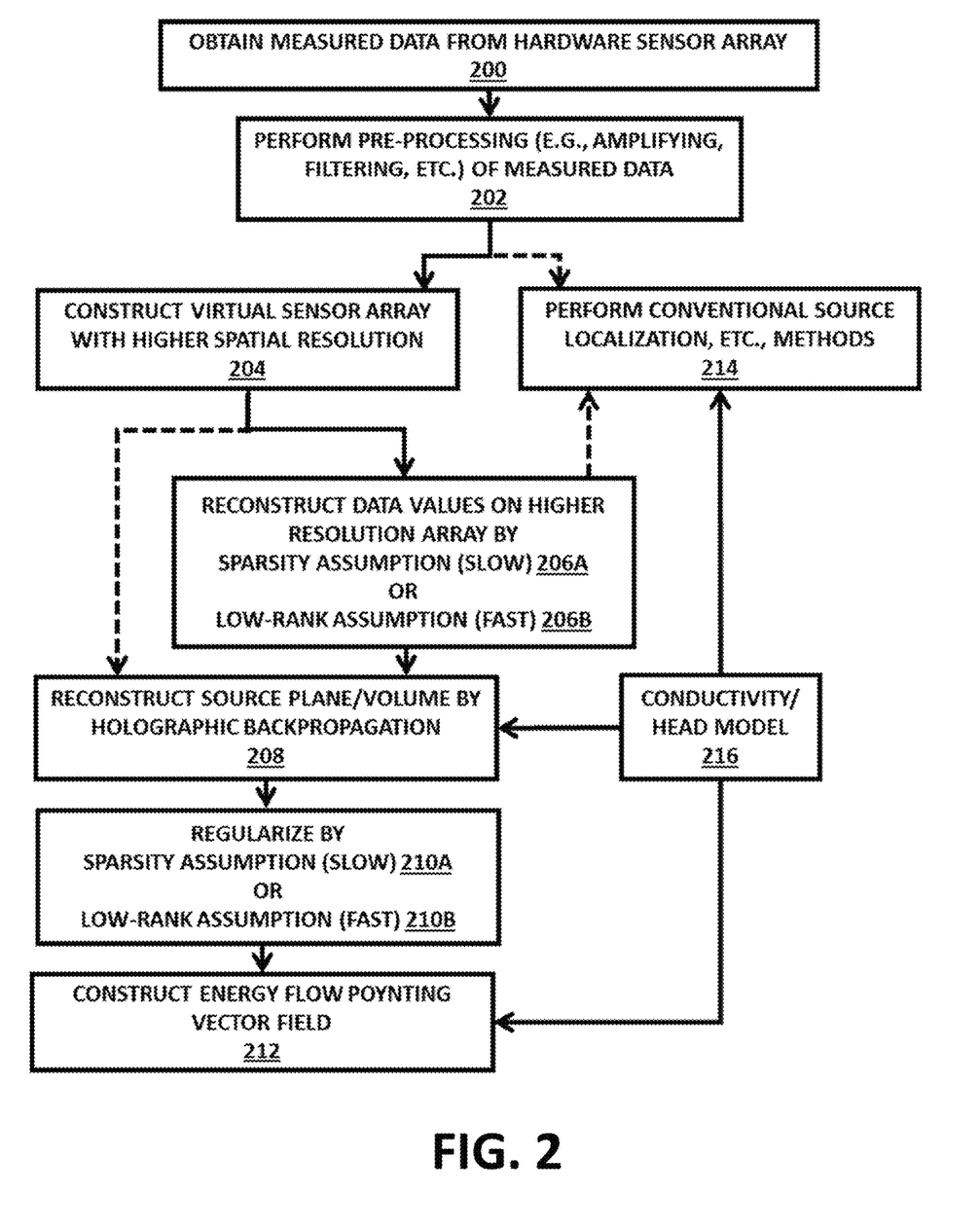
FIG. 2 is a flowchart illustrating a super-resolution method in accordance with some embodiments.

FIG. 2 is a flowchart illustrating a method for super-resolution from far-field recordings in accordance with some embodiments. In step 200, raw measurement data is obtained from an imaging array (see FIGS. 3A and 3C for examples). In step 202, the measurement data undergoes pre-processing, such as amplifying, filtering, de-trending, etc. In step 204, a virtual sensor array with higher resolution than the original hardware array is constructed (see FIG. 3B for an example). In step 206, near-field information is reconstructed under an assumption of either sparsity (step 206A) or low-rank approximation (step 206B (see FIG. 3B for an example of the latter). If recordings are already in the near-field, step 206 may be skipped. In step 208, holographic backpropagation is used to amplify and/or focus the near-field information and reconstruct the source plane and/or volume. In step 210 the holographic backpropagation is regularized by assuming sparsity or low-rank approximation, ultimately extending super-resolution to the depth axis as well. In step 212, the energy flow Poynting vector field is constructed as the cross-product of the reconstructed electric and magnetic fields (see FIG. 4C for an example). In some embodiments, conventional methods 214 may be employed with the reconstructed higher resolution data, but with lower depth resolution than provided by steps 208 and 210A or 210B. A conductivity or head model 216 (i.e., a 3D layout of the conductivity of the brain and skull), whether generic or patient/population-specific (e.g., MRI-based), may be used in any of steps 208, 212, and 214.

Figure 3A:
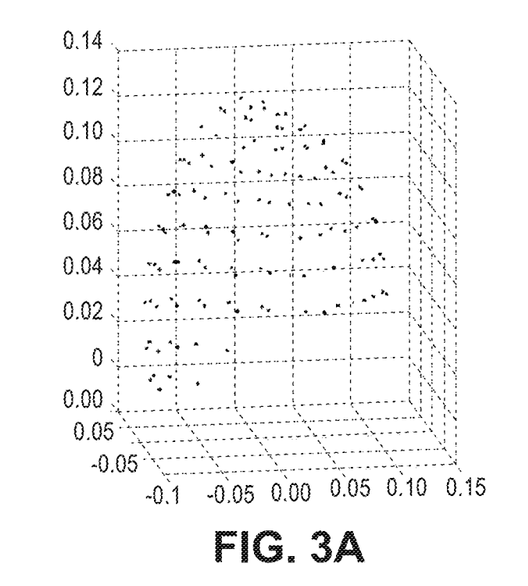
FIGS. 3A-3D are plots illustrating examples of an original sensor array layout, a higher resolution virtual sensor layout, raw measured data, and reconstructed data, respectively, in accordance with some embodiments.
Figure 3B:
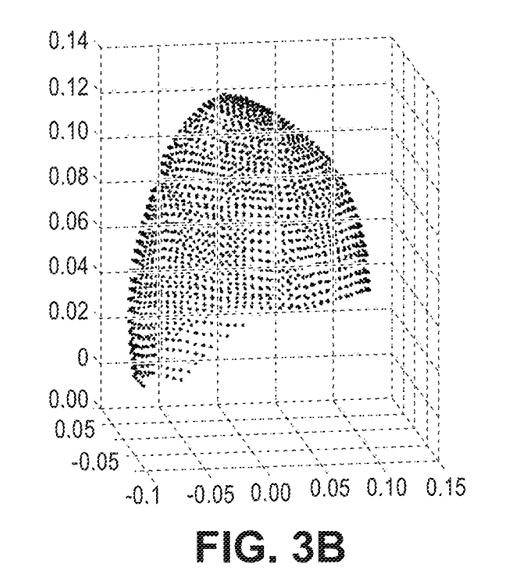
Figure 3C:
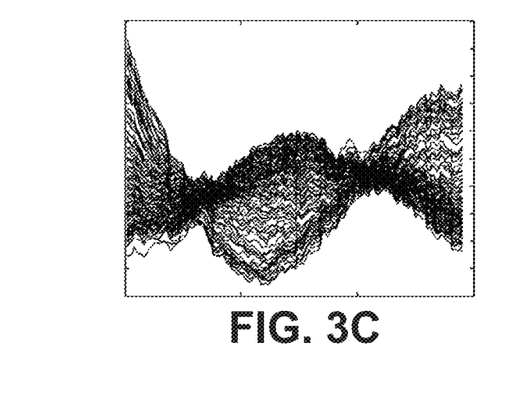
Figure 3D:
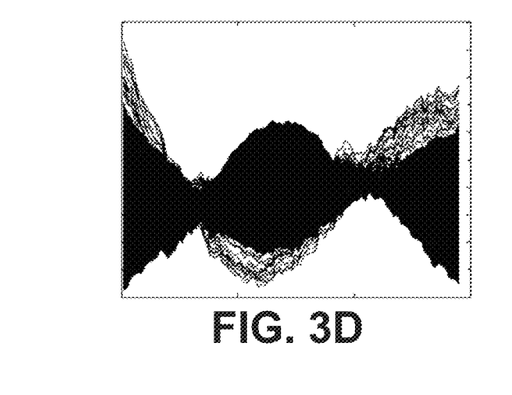

FIG. 3A provides an example of an original array layout of hardware sensors, which may be compared to the corresponding increased number (for higher resolution) of sensors in a virtual array shown in FIG. 3B. Raw data measured using the hardware sensor array in FIG. 3A is plotted in FIG. 3C, while the reconstructed data obtained using the virtual sensor array in FIG. 3B is plotted in FIG. 3D.

Figure 4A:
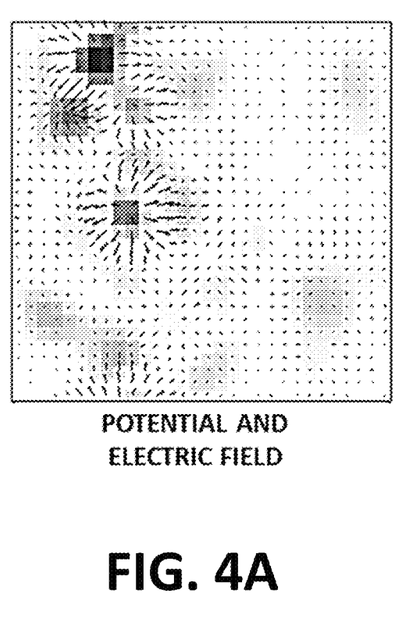
FIGS. 4A-4C are images illustrating real recorded potential and electric fields; reconstructed potential, electric, and magnetic fields; and reconstructed potential, electric, magnetic, and Poynting vector fields and their relations according to the right-hand rule, respectively, in accordance with some embodiments.
Figure 4B:
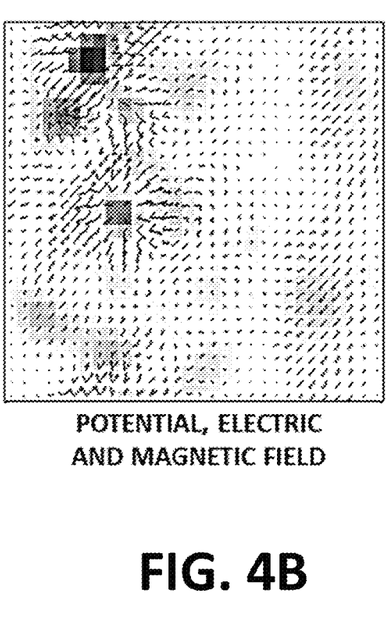
Figure 4C:
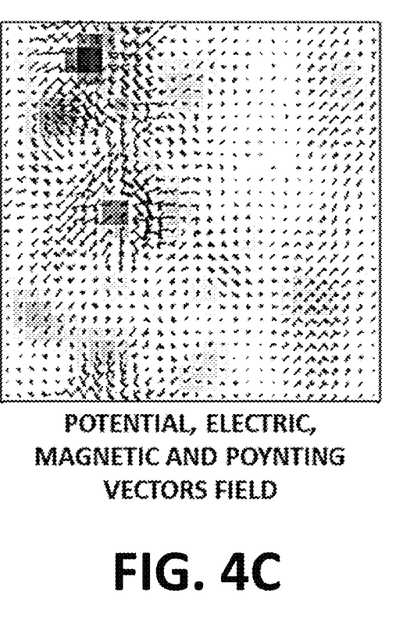

FIG. 4A is an image illustrating real recorded potential and electric fields; FIG. 4B is an image illustrating reconstructed potential, electric, and magnetic fields; and FIG. 4C is an image illustrating reconstructed potential, electric, magnetic, and Poynting vector fields and their relations according to the right-hand rule in accordance with some embodiments. The energy flow Poynting vector field in FIG. 4C may be reconstructed volumetrically and/or by section as the cross-product of the electric field and the magnetic field. When only one of these fields is recorded, the other field is estimated by application of a model of material properties (e.g., conductivity, permeability, and permittivity) of the neural tissue and other tissue in the volume of interest (see also step 212 of the method in FIG. 2). The estimated field may take into account potential inhomogeneity in the tissue.

Figure 5A:
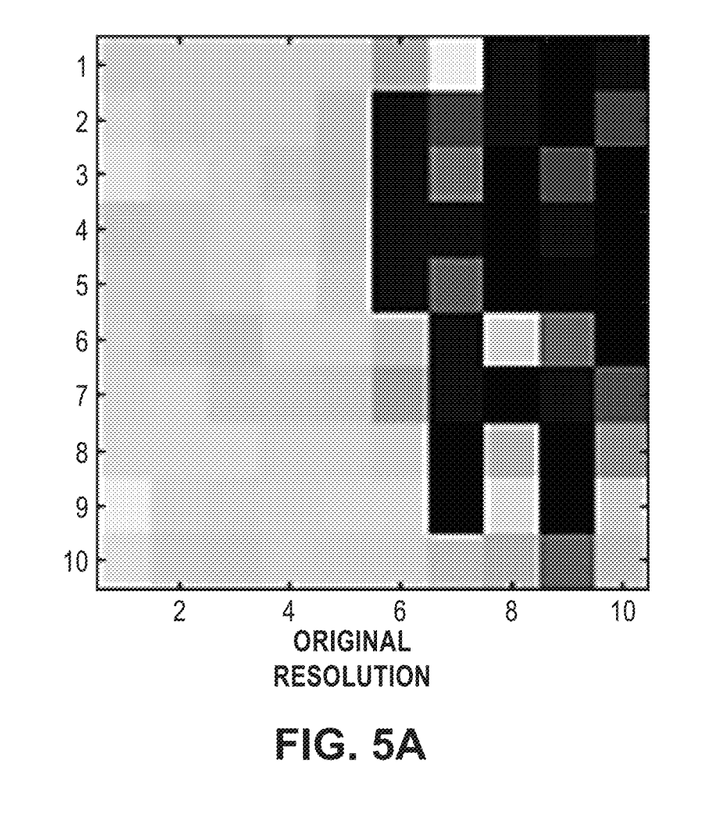
FIGS. 5A and 5B are energy source density graphs illustrating superior resolution and neural focal point localization in accordance with some embodiments.
Figure 5B:
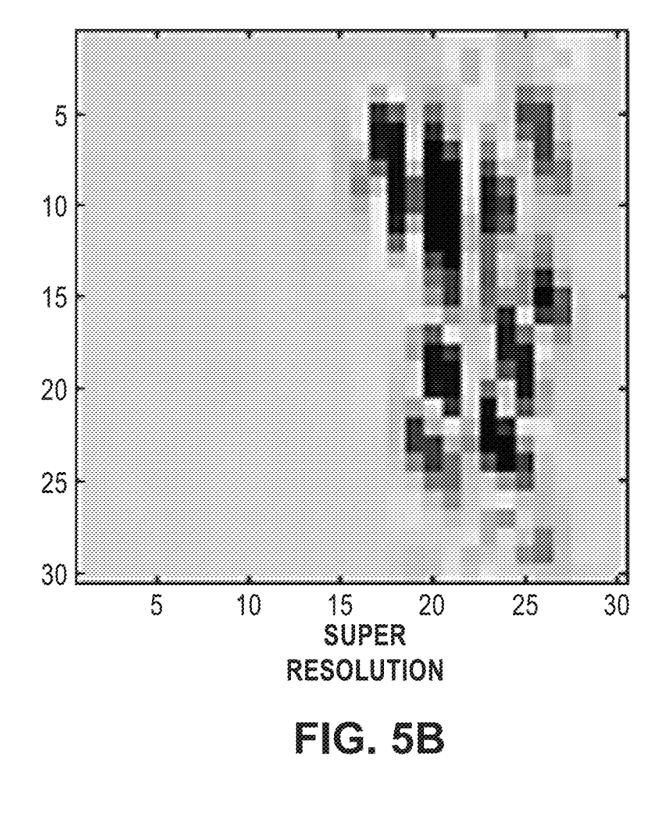
Figure 6A:
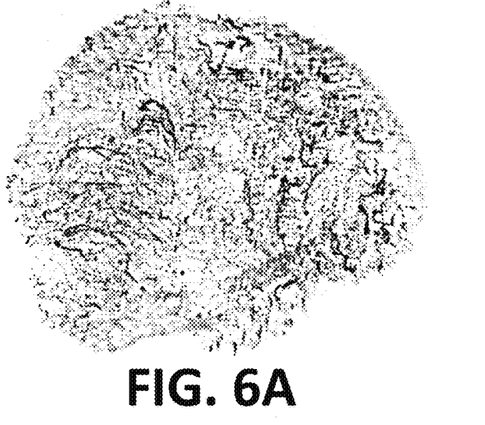
FIGS. 6A-6F are top, bottom, and side views illustrating 3D full-brain volumetric reconstruction of the energy flow Poynting vector field in accordance with some embodiments.
Figure 6B:
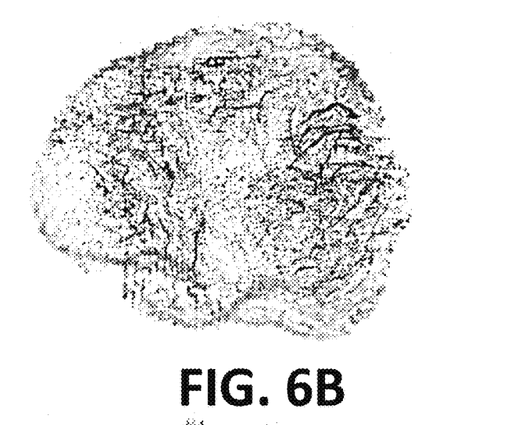
Figure 6C:
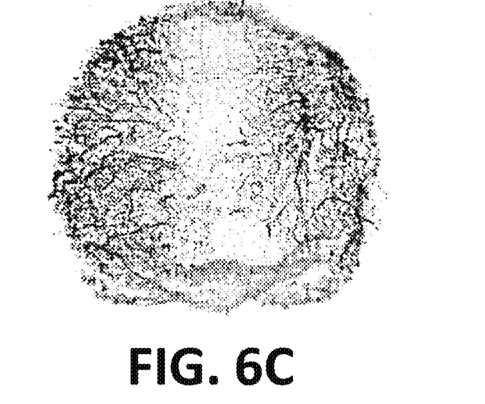
Figure 6D:
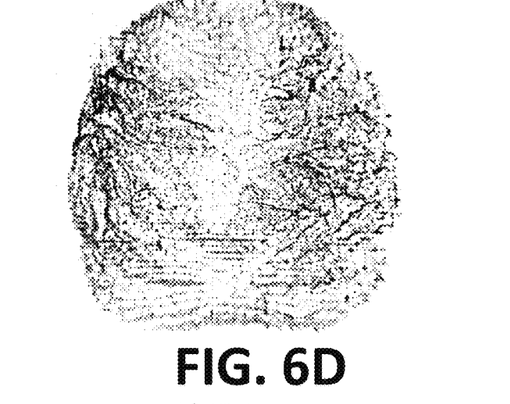
Figure 6E:
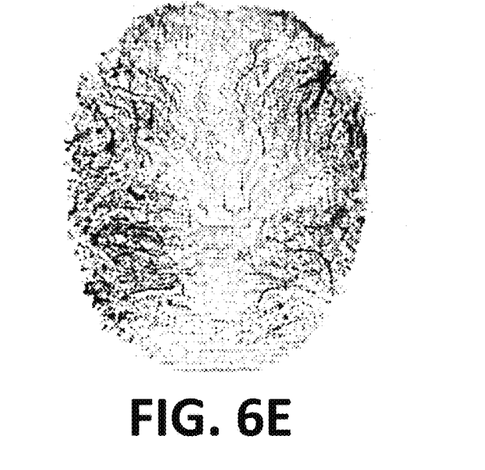
Figure 6F:
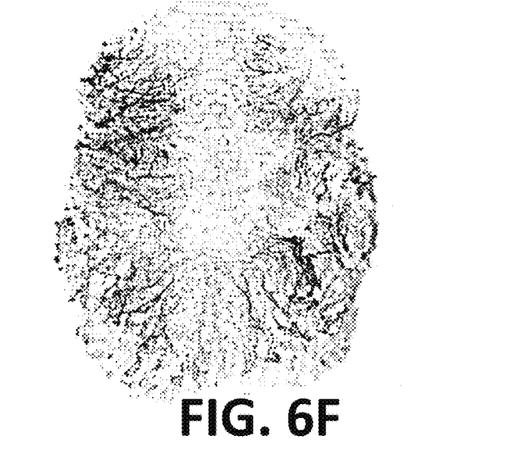

The energy source density is the divergence of the energy flow Poynting vector field, and the energy dissipation as the dot-product of the electric-field with itself and the conductivity. FIGS. 5A-5B are a series of energy source density graphs illustrating a typical improvement in source (and sink) localization from increased resolution of energy source density on real neural data in a 2D depth plane in accordance with some embodiments. The super resolution of the plane shown in FIG. 5B provides much more detail than the original resolution of the same plane shown in FIG. 5A.

FIG. 6A-6F are top, bottom, and side views illustrating 3D volumetric reconstruction of the energy flow Poynting vector field in a real human brain, based on EEG recorded using the layout illustrated in FIG. 3A, and with increased resolution using the virtual sensor array illustrated in FIG. 3B, following the reconstruction pathway of FIG. 2, specifically steps 200, 202, 204, 206B, 208 (using model 216), 210B, and 212 (using model 216). As an example, the energy flow Poynting vector field is reconstructed within a space of 100×100×100 units, or one million voxels, equal to one million unique 3D vectors. The vector field in FIGS. 6A-6F may be visualized by one million particles that follow and trace the vector field to reveal the resulting flow of energy. For practical reasons, a single time-frame is shown in grayscale.

Some embodiments may be implemented using various recording equipment with multiple simultaneous recording channels. The channels may be arranged according to a specific geometry in some embodiments. Other embodiments may not require a specific geometry. For example, a simplified implementation may include one or more uniform plane arrays and/or random geometries for improved sparsity properties.

In some embodiments, neural source localization, including early change-detection (since smaller changes can be detected), is improved. Early change-detection may lead to better patient outcomes in dementia, particularly age-related dementia like Alzheimer's disease, in which early treatment improves prognosis.

In additional embodiments, causality estimation between neural sources and sinks (e.g., focal points of seizures) is improved. Improved focal point localization may lead to better surgical outcomes, for example, by more accurately pinpointing epileptic tissue and by minimizing excess tissue removal.

In further embodiments, energy-based measures may distinguish between conventional neurotransmission types (e.g., synaptic transmissions, gap junctions, and field-based ephaptic connections) by breaking the energy flow Poynting vector field down into its geometric constituents.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety, including but not limited to the following:

Henrik D. Kjeldsen, et al., "Near-field Electromagnetic Holography for High-Resolution Analysis of Network Interactions in Neuronal Tissue," J. Neuroscience Methods 253 (2015) 1-9 (attached hereto as Exhibit A).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A system for super-resolving electromagnetic neuro-imaging, the system comprising:
    at least one multi-channel recording device for capturing data including at least one of electric field data and magnetic field data in neural tissue of a subject over a period of time, the at least one multi-channel recording device having a first resolution;
    at least one memory to record the captured data and to store processor executable instructions; and
    at least one processor coupled to the at least one multi-channel recording device and the at least one memory, wherein upon execution of the processor executable instructions by the at least one processor, the at least one processor:
        applies holographic backpropagation to the captured data, the holographic backpropagation constrained by at least one of sparsity and low-rank approximation in at least one of a near-field and a far-field;
        reconstructs electromagnetic energy flow information at a second resolution in one iteration, the electromagnetic energy flow information comprising a Poynting vector, the second resolution being higher than the first resolution in at least two of three spatial dimensions; and
        generates, based on the electromagnetic energy flow information at the second resolution, data indicating at least one of a neural energy source location, a neural energy sink location, and a neural causality relation.

2. The system of claim 1, wherein the neural causality relation distinguishes contact-based neural transmission and field-based neural transmission.

3. The system of claim 1, wherein the at least one multi-channel recording device includes a near-field multi-channel recording device.

4. The system of claim 1, wherein the at least one multi-channel recording device includes a far-field multi-channel recording device.

5. The system of claim 1, wherein the at least one multi-channel recording device includes at least one of a microelectrode array (MEA) device, an electroencephalography (EEG) device, an electrocorticography (ECoG) device, and a magnetoencephalography (MEG) device.

6. The system of claim 1, wherein the electromagnetic energy flow information comprises more than one Poynting vector.

7. The system of claim 1, wherein the causality relation is a flow direction of the Poynting vector field.

8. A system for super-resolving electromagnetic localization, the system comprising:
    at least one multi-channel recording device for capturing data including at least one of electric field data and magnetic field data over a period of time, the at least one multi-channel recording device having a first resolution;
    at least one memory to record the captured data and to store processor executable instructions; and
    at least one processor coupled to the at least one multi-channel recording device and the at least one memory, wherein upon execution of the processor executable instructions by the at least one processor, the at least one processor:
        applies holographic backpropagation to the captured data, the holographic backpropagation constrained by at least one of sparsity and low-rank approximation in at least one of a near-field and a far-field;
        reconstructs electromagnetic energy flow information at a second resolution in one iteration, the electromagnetic energy flow information comprising a Poynting vector, the second resolution being higher than the first resolution in at least two of three spatial dimensions; and
        generates, based on the electromagnetic energy flow information at the second resolution, data indicating at least one of an energy source location, an energy sink location, and a causality relation.

9. A system for super-resolving electromagnetic localization, the system comprising:
    at least one communication interface;
    at least one memory to record the captured data and to store processor executable instructions; and
    at least one processor coupled to the at least one communication interface and the at least one memory, wherein upon execution of the processor executable instructions by the at least one processor, the at least one processor:
        obtains, via the at least one communication interface, the captured data including at least one of electric field data and magnetic field data captured over a period of time by at least one multi-channel recording device, the at least one multi-channel recording device having a first resolution;
        applies holographic backpropagation to the captured data, the holographic backpropagation constrained by at least one of sparsity and low-rank approximation in at least one of a near-field and a far-field;
        reconstructs electromagnetic energy flow information at a second resolution in one iteration, the electromagnetic energy flow information comprising a Poynting vector, the second resolution being higher than the first resolution in at least two of three spatial dimensions; and generates, based on the electromagnetic energy flow information at the second resolution, data indicating at least one of an energy source location, an energy sink location, and a causality relation.

10. A method for super-resolving electromagnetic neuroimaging, the method comprising:

obtaining captured data including at least one of electric field data and magnetic field data from neural tissue of a subject over a period of time by at least one multi-channel recording device, the at least one multi-channel recording device having a first resolution;

applying, via at least one processor, holographic backpropagation to the captured data, the holographic backpropagation constrained by at least one of sparsity and low-rank approximation in at least one of a near-field and a far-field;

reconstructing, via the at least one processor, electromagnetic energy flow information at a second resolution in one iteration, the electromagnetic energy flow information comprising a Poynting vector, the second resolution being higher than the first resolution in at least two of three spatial dimensions; and generating, via the at least one processor, data indicating at least one of a neural energy source location, a neural energy sink location, and a neural causality relation based on the electromagnetic energy flow information at the second resolution.

11. The method of claim 10, wherein the neural causality relation distinguishes contact-based neural transmission and field-based neural transmission.

12. The method of claim 10, further comprising:

capturing, via the at least one multi-channel recording device, the captured data including at least one of electric field data and magnetic field data.

13. The method of claim 10, wherein the at least one multi-channel recording device includes a near-field multi-channel recording device.

14. The method of claim 10, wherein the at least one multi-channel recording device includes a far-field multi-channel recording device.

15. The method of claim 10, wherein the at least one multi-channel recording device includes at least one of a microelectrode array (MEA) device, an electroencephalography (EEG) device, an electrocorticography (ECoG) device, and a magnetoencephalography (MEG) device.

16. The method of claim 10, wherein the electromagnetic energy flow information comprises at least one Poynting vector.

17. The method of claim 10, wherein the causality relation is a flow direction of the Poynting vector field.

18. A method for super-resolving electromagnetic localization, the method comprising:

obtaining captured data including at least one of electric field data and magnetic field data captured over a period of time by at least one multi-channel recording device, the at least one multi-channel recording device having a first resolution;

applying holographic backpropagation to the captured data, the holographic backpropagation constrained by at least one of sparsity and low-rank approximation in at least one of a near-field and a far-field;

reconstructing electromagnetic energy flow information at a second resolution in one iteration, the electromagnetic energy flow information comprising a Poynting vector, the second resolution being higher than the first resolution in at least two of three spatial dimensions; and generating data indicating at least one of an energy source location, an energy sink location, and a causality relation based on the electromagnetic energy flow information at the second resolution.

* * * * *